United States Patent [19]

Huband

[11] Patent Number: 5,104,385
[45] Date of Patent: Apr. 14, 1992

[54] PROTECTIVE NEEDLE ASSEMBLY FOR HYPODERMIC SYRINGE

[76] Inventor: Michael L. Huband, 6513 Hagueman Dr., Richmond, Va. 23225

[21] Appl. No.: 711,652

[22] Filed: Jun. 6, 1991

[51] Int. Cl.⁵ .............................................. A61M 5/32
[52] U.S. Cl. ................................... 604/198; 604/263
[58] Field of Search ................ 604/198, 263, 192, 187

[56] References Cited

U.S. PATENT DOCUMENTS

| | | | |
|---|---|---|---|
| 4,737,144 | 4/1988 | Choksi | 604/198 |
| 4,911,693 | 3/1990 | Paris | 604/192 |
| 4,923,447 | 5/1990 | Morgan | 604/198 |
| 4,935,016 | 6/1990 | Deleo | 604/263 X |
| 4,994,045 | 2/1991 | Ranford | 604/198 |

Primary Examiner—John D. Yasko
Attorney, Agent, or Firm—Norman B. Rainer

[57] ABSTRACT

A protective needle assembly adapted to be mounted upon the discharge extremity of the barrel of a conventional hypodermic syringe has a cylindrical hub that holds an axially aligned cannula needle. A transparent cylindrical sheath slidingly engages the hub. The sheath has a longitudinal slot and communicating detent, and a locking aperture. A tab radially emergent from the hub can be caused to engage the detent, slot or locking aperture, achieving respectively, a storage state where the sheath extends forwardly of the tip of the needle, a use state where the tip of the needle extends forwardly of the sheath, and an irreversibly locked disposal state wherein the sheath is forward of the tip of the needle.

6 Claims, 1 Drawing Sheet

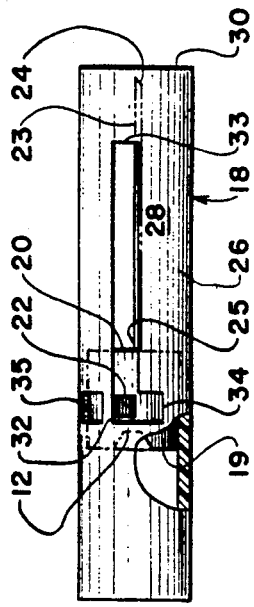
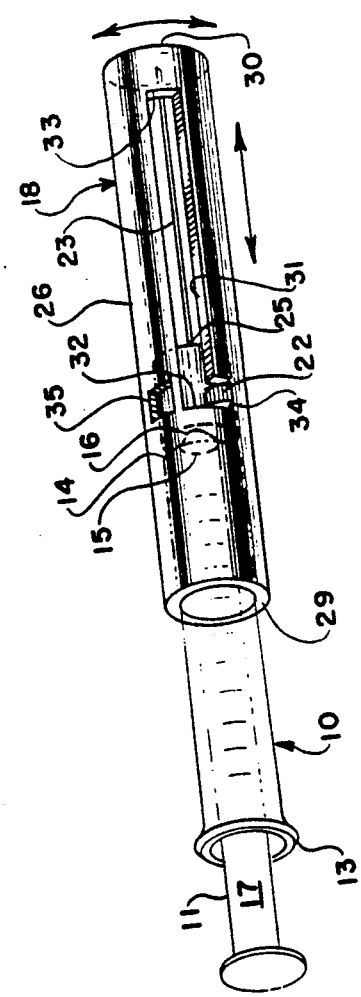
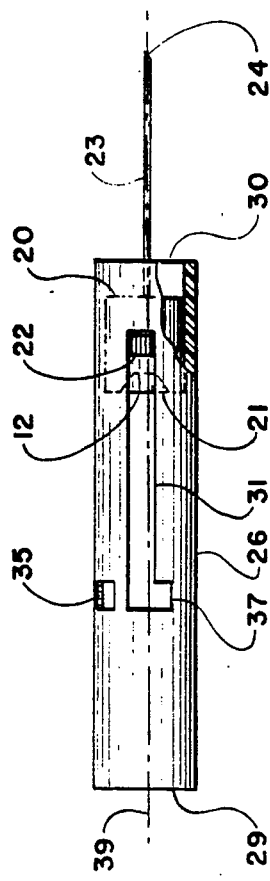
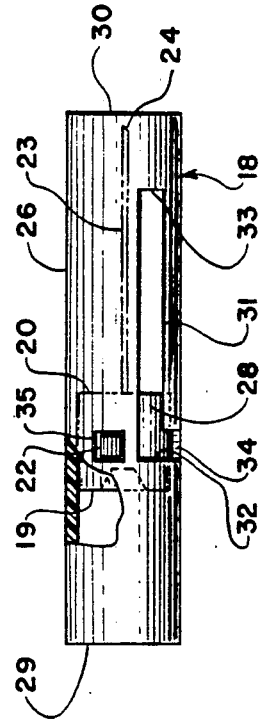
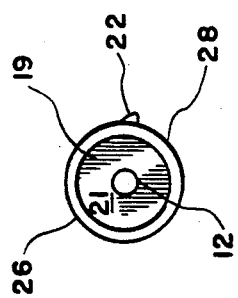

PROTECTIVE NEEDLE ASSEMBLY FOR HYPODERMIC SYRINGE

BACKGROUND OF THE INVENTION

1. Field of the Invention

This invention relates to hypodermic syringes, and more particularly concerns a needle assembly adapted to protect people using hypodermic syringes from accidental needle sticks, and further to render used needles unusable.

2. Description of the Prior Art

Health professionals and others who use hypodermic syringes to inject medicine or other substances into patients or to obtain samples of blood or other bodily fluids from people are subject to risk of infection if they are stuck with a contaminated needle that has been withdrawn from an infected person. This is a matter of special concern when facing the possibility of dealing with patients who have infectious hepatitis or Acquired Immune Deficiency Syndrome (AIDS), but it is preferable to avoid or minimize the possibility of infection with any disease. The needle of a hypodermic syringe, being sharp to penetrate the skin readily for its intended purpose, is a threat to penetrate clothing and rubber gloves of the health professional using the hypodermic syringe and thus to puncture the skin of the health professional. The threat of contamination is present with needles that are used for subcutaneous and intramuscular injection, but it is particularly threatening with needles used for intravenous injection of and for the drawing of blood or other body fluids from veins or other parts of the body. Likewise, hypodermic syringes used in dentistry also pose a threat of accidental contamination.

A hypodermic syringe is herein defined as a combination of a hollow needle or cannula anchored in a hub, and a syringe comprised of a plunger slidingly interactive with a fluid-confining transparent barrel that releasibly engages the hub. If the hypodermic syringe is designed for injection or withdrawal using positive pressure or vacuum produced by the plunger, then the needle normally terminates in the hub. The barrel is typically marked with graduations to measure quantities of fluids injected or withdrawn. If the hypodermic syringe is designed for use in a vacuum withdrawal system or for dental use, then the needle is normally double-ended, passing completely through the hub and extending beyond the hub in both directions. The hypodermic syringe in this case serves as a support for a medication carpule having a soft plastic that is pierced by the needle, thereby enabling the plunger to dispense the contents of the carpule. In either event, the forwardly protruding needle is normally equipped with a removable cover to protect health professionals from accidental contact with the point of the needle.

For any of the uses described above, universal practice is either to discard the needle after one use, or else to sterilize it before another use. During the act of disposal, the contaminated needle is exposed between its site of use and a dispenser device. Carelessness on the part of the health professional or other user of the hypodermic, distractions occasioned by telephone calls and the like, or accidental jostling by passersby, all make it possible to bring the contaminated point of the needle into contact with the body of the health professional. A particular threat exists when the needle cover is replaced before the needle is discarded. In this case the health professional typically holds the needle cover in one hand and inserts the needle into an opening in the cover. The same distracting factors may cause the contaminated point of the needle to come into contact with his or her hand.

The danger described above has been the subject of several patents. Strauss, U.S. Pat. No. 4,664,654, "Automatic Protracting and Locking Hypodermic Needle Guard" is an example of one means for protecting the tip of a contaminated needle. Strauss teaches a spring-activated sliding member that covers the needle. The sliding member can be locked in place to protect the point of the needle from coming in contact with anything. When the sliding member is unlocked, the needle is exposed for use. The sliding member is placed against the skin after the needle is inserted. The spring maintains force on the sliding member, and restores it to the protective position when the needle is withdrawn. The device taught by Strauss has the disadvantage of being relatively complex mechanically, which increases it manufacturing cost, and also of coming in contact with the skin of a patient. In addition, the device taught by Strauss is limited to use for subcutaneous and intramuscular injection or for the drawing of blood samples.

U.S. Pat. No. 4,139,009 to Alvarez discloses a retractable needle cover which is comprised of a hub member and a sliding member joined by a multiplicity of resilient arms to maintain the distance along the needle between the hub and sliding members. The arms are bowable away from the needle and are splayed outward upon retraction of the sliding member to allow penetration of body tissue. However, the splayed arms render the device impractical for usage in dentistry as the splayed arms prohibit use in the tight confines of the oral cavity.

U.S. Pat. Nos. 4,702,738 and 4,801,295 to Spencer discloses an integral system in which the needle, syringe and protective cover are interactive in use. The protective device does not lend itself toward usage with standard syringes and commonly available needles. The device disclosed by Laico in U.S. Pat. No. 4,892,521 utilizes either guide rods or telescopic tubes in order to maintain the locked position of the needle covering device. Such guide means constitute additional moving parts, causing complexity of use and high manufacturing cost.

U.S. Pat. No. 4,863,436 to Glick discloses a hypodermic syringe having a protection device comprising a long hub which slidingly supports a first cylindrical cover. A second cover is employed to lock the first cover in place. The device does not shield both ends of a double-ended needle such as those used in dentistry. The hub effectively increases the length of the hypodermic syringe, thereby causing cumbersome operation. The necessary minipulation of the second cover makes the device difficult to use.

It is therefore an object of the present invention to provide a protective covering device for the cannula needle of a hypodermic syringe.

It is another object of the present invention to provide a needle covering device of the aforesaid nature which is adaptable to a multiplicity of currently available hypodermic syringes.

It is yet another object of the present invention to provide a device of the aforesaid nature which will effectively cover both ends of a double-ended cannula needle when detached from a syringe.

It is still another object of the present invention to provide a needle covering device of the aforesaid nature which has a minimal number of moving parts, is simple to use and amenable to low cost manufacture.

SUMMARY OF THE INVENTION

The above and other beneficial objects and advantages are accomplished in accordance with the present invention by a protective needle assembly adapted for use with a conventional hypodermic syringe comprised of a barrel having a discharge extremity provided with needle-accepting means, said needle assembly comprising:

a) a hub bounded by a circular cylindrical sidewall perimeter having a center axis and a diameter slightly greater than the diameter of said barrel, a distal extremity, and a proximal extremity interactive with said needle accepting means, and having a control tab radially emergent from said perimeter, b) a cannula needle having a pointed forward extremity and a rear portion penetrating said hub upon said axis, and c) a transparent cylindrical sheath elongated between forward and rearward rims and configured to slide upon said sidewall perimeter and envelope said hub, barrel and needle, said sheath having: 1) a longitudinal slot extending in parallel relationship to said axis between a first extremity and a second extremity forwardly spaced from said first extremity, 2) a circumferentially disposed arcuate slot communicating with said first extremity, and 3) a locking aperture circumferentially separated from said arcuate slot, d) said sheath engaging said control tab in a manner whereby reciprocal axial motion of the sheath is permitted when said tab is in said longitudinal slot, and an irreversibly locked condition is produced when the tab is in said locking aperture, said locked condition characterized in disposing the forward rim of the sheath forwardly of the pointed extremity of the needle.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 1 is a perspective view of an embodiment of the needle assembly of the present invention in its storage or protected state and shown in functional association with a conventional hypodermic syringe.

FIG. 2 is a side view of the embodiment of FIG. 1 in its ready to use state.

FIG. 3 is a side view of the embodiment of FIG. 1 in its deployed state.

FIG. 4 is a side view of the embodiment of FIG. 1 in its locked, disposal state.

FIG. 5 is an end view of the embodiment of FIG. 1.

DESCRIPTION OF THE PREFERRED EMBODIMENT

Referring to FIGS. 1-5, an embodiment of the protective needle assembly of the present invention is shown adapted for use with common hypodermic syringe 10 comprised of elongated cylindrical barrel 11 having open receiving extremity 13, and discharge extremity 14 having centered aperture 15 and associated needle mounting means in the form of conically shaped nipple 16. Elongated plunger 17 is adapted to reciprocate in close conformity within barrel 11.

Needle assembly 18 is comprised of monolithic cylindrical hub 19 defined in part by cylindrical sidewall 28 having a center axis 39 and a diameter slightly greater than the diameter of barrel 11. Said hub is further bounded by substantially flat distal extremity 20, and proximal extremity 21 having a socket 12 centered on said axis and adapted to receive nipple 16 of barrel 11. Socket 12 may be configured to receive needle mounting means of conical shape, which engages the hub by frictional effect, or may be threaded or otherwise configured to receive needle mounting means which lock by mechanical features such as threads in a twisting motion. A control tab 22 emerges radially from said cylindrical sidewall.

Cannula needle 23 has a pointed forward extremity 24 and a rear portion 25 which penetrates said hub on said axis and terminates in communication with socket 12.

A transparent cylindrical sheath 26 elongated between forward and rearward rims 30 and 29, respectively is configured to slidingly embrace the hub, barrel and needle by virtue of frictional interaction with sidewall 28 of said hub. The sheath has a longitudinal slot 31 extending in parallel relationship to said axis between a first extremity 32, and a second extremity 33 forwardly spaced from said first extremity. A circumferentially disposed arcuate slot 34 communicates at one terminus with said first extremity in an L-shaped intersection. The opposite terminus of slot 34, designated 37 serves as a retaining shoulder, or detent, as will hereinafter be shown. A locking aperture 35 is spaced apart from slot 34 in circumferential alignment therewith. The expression "transparent" as employed herein is intended to encompass sheaths fabricated of transparent plastic, and sheaths fabricated of opaque material but possessing slots that permit visual observation of the volumetric markings on the barrel of the hypodermic syringe.

In its stored or protective state, the needle assembly will be as shown in FIG. 1 wherein tab 22 resides within retaining shoulder 37. In this configuration, the forward rim of the sheath extends forwardly of the pointed extremity of the needle. By twisting the sheath about the hub, tab 22 can be made to reside within slot 31, as shown in FIGS. 2 and 3. In this condition, a ready state, sheath 26 can undergo axially reciprocal movement in sliding engagement with the hub. At one extremity of said sliding movement, as shown in FIG. 3, substantially the entire length of sheath 26 is disposed upon barrel 11, causing the pointed extremity 24 of needle 23 to be exposed for use.

By sliding the sheath to its forward position and twisting about the axis, tab 22 enters locking aperture 35, producing the locked or disposal state of the assembly shown in Fugure 4. In said locked state, the sheath is immobilized in a position which protects the point of the needle. By causing the tab 22 to have a directional contour as a tapered gear tooth, entrance of said tab 22 into aperture 35 is irreversible, thereby preventing reuse of the needle and producing a protected condition for safe disposal.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A protective needle assembly adapted for use with a conventional hypodermic syringe comprised of a barrel having a discharge extremity provided with needle-accepting means, said needle assembly comprising:
   a) a hub bounded by a circular cylindrical sidewall perimeter having a center axis and a diameter slightly greater than the diameter of said barrel, a distal extremity, and a proximal extremity interactive with said needle accepting means, and having a control tab radially emergent from said perimeter,
   b) a cannula needle having a pointed forward extremity and a rear portion penetrating said hub upon said axis, and
   c) a transparent cylindrical sheath elongated between forward and rearward rims and configured to slide upon said sidewall perimeter and envelope said hub, barrel and needle, said sheath having: 1) a longitudinal slot extending in parallel relationship to said axis between a first extremity and a second extremity forwardly spaced from said first extremity, 2) a circumferentially disposed arcuate slot communicating with said first extremity, and 3) a locking aperture circumferentially separated and spaced from said arcuate slot, by a portion of said cylindrical sheath
   d) said sheath engaging said control tab in a manner whereby reciprocal axial motion of the sheath is permitted when said tab is in said longitudinal slot, and an irreversibly locked condition is produced when the tab is in said locking aperture, said locked condition characterized in disposing the forward rim of the sheath forwardly of the pointed extremity of the needle.

2. The protective needle assembly of claim 1 wherein said sheath is fabricated of a transparent plastic.

3. The protective needle assembly of claim 1 wherein said hub is of monolithic construction.

4. The protective needle assembly of claim 1 wherein the proximal extremity of said hub contains recessed therein a socket centered upon said axis.

5. The protective needle assembly of claim 4 wherein said socket is conically shaped.

6. The protective needle assembly of claim 4 wherein the rear portion of said needle terminates in communication with said socket.

* * * * *